United States Patent [19]

Mitchell et al.

[11] 4,230,887

[45] Oct. 28, 1980

[54] RECOVERY OF ANHYDROUS ACIDS

[75] Inventors: William T. Mitchell, Corpus Christi; Phillip S. Snyder, Houston, both of Tex.

[73] Assignee: Celanese Corporation, New York, N.Y.

[21] Appl. No.: 878,196

[22] Filed: Feb. 16, 1978

[51] Int. Cl.$^2$ .................. C07C 51/42; C07C 51/44; C07C 51/48; C07C 53/08; C07C 53/22; C07C 55/02; C07C 57/04; C07C 57/14

[52] U.S. Cl. ........................................ 562/593; 203/15; 203/16; 203/42; 203/64; 203/DIG. 21; 562/530; 562/531; 562/532; 562/534; 562/535; 562/536; 562/538; 562/545; 562/546; 562/547; 562/548; 562/549; 562/600; 562/606; 562/608

[58] Field of Search ............... 562/593, 600, 608, 606, 562/530–532, 534–536, 538, 545–549

[56] References Cited

U.S. PATENT DOCUMENTS

| | | | |
|---|---|---|---|
| 2,430,086 | 11/1947 | Staff | 562/600 |
| 2,578,698 | 12/1951 | Hanford | 562/608 |
| 2,638,481 | 5/1963 | Nachod, Jr; | 562/593 |
| 3,448,147 | 6/1969 | Hornig | 562/600 |
| 3,932,500 | 1/1976 | Duembgen et al. | 562/600 |

*Primary Examiner*—Vivian Garner
*Attorney, Agent, or Firm*—S. N. Rice; R. M. Pritchett

[57] ABSTRACT $C_2$–$C_6$ monocarboxylic and dicarboxylic acids are scrubbed from gas phase mixtures of such acids and water by gas absorption techniques utilizing a liquid solvent comprising a polyoxyalkylene glycol or a monoalkyl or dialkyl ether thereof. The solvent enriched with the acid is subjected to distillation to recover a substantially anhydrous acid product.

20 Claims, 1 Drawing Figure

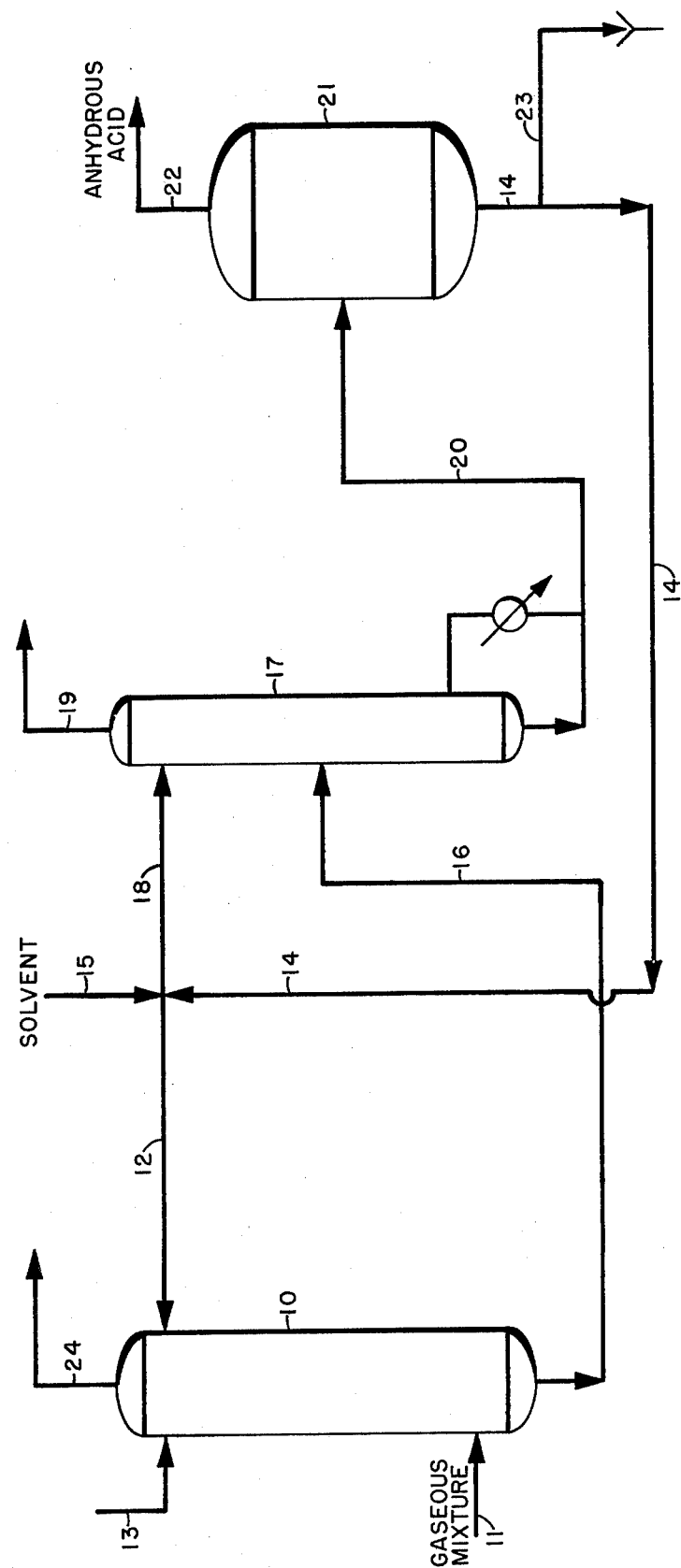

RECOVERY OF ANHYDROUS ACIDS

BACKGROUND OF THE INVENTION

Present invention relates to a process for the recovery of substantially anhydrous carboxylic acids from gaseous mixtures containing such carboxylic acids and water, and is particularly applicable to the $C_2$-$C_5$ monocarboxylic acids. Other compounds may also be present in the gaseous mixture.

In various industrial processes there results a high temperature gaseous mixture containing carboxylic acids and water, and sometimes various other compounds such as inert gases. Usually these gaseous mixtures are obtained in vapor phase oxidation processes where hydrocarbons, carbonyl compounds or alcohols or mixtures of such, are oxidized with oxygen (generally derived from air) in the presence of a catalyst to produce a carboxylic acid product. In many cases the carboxylic acid will be a mixture of different carboxylic acids depending on the reactants, reaction conditions, etc. The carboxylic acids may be saturated or unsaturated. By way of example, acrolein and/or propylene may be oxidized to produce acrylic acid; and, isobutylene and/or t-butanol may be oxidized to produce a mixture of methacrylic acid and acetic acid as the main products.

In conducting such oxidation processes, the reactants are generally diluted with inert gas and/or steam for safety reasons and for better control of the heat of reaction. The reaction gas is thus generally very lean with respect to the carboxylic acid product and contains, in addition to the desired carboxylic acid product, varying amounts of unoxidized reactants, water vapor, carbon oxides, nitrogen, and various oxygenated hydrocarbon byproducts. The economics of these processes depend in a large part on how the carboxylic acid product is recovered, particularly on how the water is eliminated and separated from the reaction gas.

Various processes for recovery of the carboxylic acid products from gaseous mixtures including water as a component are disclosed in the prior art. For example, U.S. Pat. No. 3,932,500 issued Jan. 13, 1976 to Gerd Duembgen, et al. discloses the recovery of acrylic acid from gaseous mixtures obtained in the vapor phase oxidation of propylene and/or acrolein by scrubbing the gaseous mixture with a hydrophobic solvent (while avoiding the formation of an aqueous phase) so as to absorb the acrylic acid into the solvent. Specific solvents disclosed include hydrocarbons and diphenyl ether. Also, U.S. Pat. No. 3,868,417 issued Feb. 25, 1975 to Gerd Duembgen, et al. discloses recovery of acrylic acid from gaseous mixtures by absorption techniques utilizing esters of carboxylic acids. Even though these methods and other prior art methods may be used to advantage, they suffer various drawbacks. For example, the process disclosed in U.S. Pat. No. 3,932,500 does not effect separation of any acetic acid that may be present with the acrylic acid in the reaction gas. New and better processes are thus constantly being sought by the industry.

It is thus an object of the present invention to provide a process for separation and recovery of a substantially anhydrous carboxylic acid product from gaseous mixtures containing such carboxylic acids and water. It is an additional object of the present invention to provide a process for treatment of a reaction gas obtained from the vapor phase oxidation of hydrocarbons and/or oxygenated hydrocarbons and containing carboxylic acid product therein so as to recover a substantially anhydrous carboxylic acid product therefrom. Additional objects will become apparent from the following description of the present invention.

SUMMARY OF THE INVENTION

The foregoing and other objects are accomplished by the present invention which in one of its aspects is a process for recovering a $C_2$-$C_6$ carboxylic acid from a gaseous mixture comprising said carboxylic acid and water, said carboxylic acid being a monocarboxylic acid or a dicarboxylic acid and being composed only of carbon, hydrogen and oxygen, said process comprising: (a) in a gas absorption zone, intimately contacting said gaseous mixture, while maintained in the vapor phase, with a solvent which is maintained in the liquid phase whereby $C_2$-$C_6$ carboxylic acid is absorbed from said gaseous mixture into said solvent, said solvent comprising a polymer of the formula:

$$R_1-O-(X)-R_2 \qquad \text{I}$$

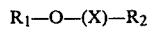

wherein $R_1$ and $R_2$ may be alike or different and are hydrogen or alkyl groups of 1 to 20 carbon atoms, and wherein X is a divalent polyoxyalkylene radical consisting essentially of repeating oxyalkylene units of the forumula:

$$-(CH_2-CH-O)- \qquad \text{II}$$
$$\qquad\quad |$$
$$\qquad\quad R_3$$

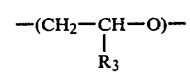

wherein $R_3$ is hydrogen or a lower alkyl radical of from 1 to 6 carbon atoms and wherein $R_3$ may be alike or different on the several repeating oxyalkylene units, said polymer having a molecular weight within the range of about 250 to 5,000, the intimate contact of said gaseous mixture and said solvent being accomplished at a temperature which is below the boiling point of said solvent at the pressure involved and which is above the dew point of said gaseous mixture at the pressure involved so as to prevent condensation of the water from said gaseous mixture; and, (b) removing from said gas absorption zone a liquid, acid enriched solvent fraction consisting essentially of said solvent having $C_2$-$C_6$ carboxylic acid absorbed therein, and recovering $C_2$-$C_6$ carboxylic acid from said solvent fraction.

DETAILED DESCRIPTION OF THE INVENTION

The heart of the present invention resides in the discovery that a polymer of Formula I above, that is the polyoxyalkylene glycols and monoalkyl and dialkyl ethers thereof, will serve as a selective solvent to absorb carboxylic acids, particularly $C_2$-$C_5$ monocarboxylic acids, from gaseous mixtures containing such acids and water. The carboxylic acids may then be recovered from the solvent such as by distillation. The polymer utilized as solvent may be of a nature which is substantially water insoluble (hydrophobic), substantially water soluble (hydrophillic) or some degree in between. The hydrophobic or hydrophillic nature of the polymer is controlled mainly by the nature of the repeating oxyalkylene units, although the end groups, $R_1$ and $R_2$, may also affect the water solubility, particularly in the lower molecular weight polymers. More specifically, the more oxyethylene units (those wherein $R_3$ is hydrogen) contained in the divalent polyoxyalkylene radical X, the more hydrophillic or water soluble the polymer will be, with the most hydrophillic polymer of the type being a polyoxyethylene glycol. The presence of oxyalkylene units wherein $R_3$ is an alkyl radical, for example oxypropylene units wherein $R_3$ is methyl, contribute to water insolubility and tend to make the polymer more hydrophobic in nature. Those polymers of Formula I above wherein $R_3$ on all of the repeating oxyalkylene units is an alkyl group will be hydrophobic in nature, for example polyoxypropylene glycol.

As stated above, $R_3$ may be hydrogen or a lower alkyl radical of from about 1 to 6 carbon atoms, such alkyl radicals including methyl, ethyl, butyl, hexyl, etc. $R_3$ does not have to be the same on each repeating unit but can be different on the several units. For example on some of the units $R_3$ could be methyl, on some units ethyl, on some units hydrogen, and the like. Where all of the $R_3$ radicals of the polymer are not the same, the oxyalkylene units containing the different $R_3$ radicals can be in block form or randomly mixed. Where $R_3$ is an alkyl radical, it is preferably a methyl radical such that the oxyalkylene unit is an oxypropylene unit. Where all of the $R_3$ radicals are not the same, it is preferred that they be randomly mixed. Solvents of the present invention include polymers of formula I wherein from about 10 to 90% of the repeating oxyalkylene units are oxyethylene and the remaining 10 to 90% of said repeating oxyalkylene units are oxypropylene units.

Specific polyoxyalkylene glycols which may be utilized as the solvent of the present invention includes polyoxyethylene glycol homopolymer, polyoxyethylene-polyoxypropylene glycol copolymer, polyoxypropylene-polyoxybutylene glycol co-polymer, the monobutyl ether of a random polyoxyethylene-polyoxypropylene glycol co-polymer, and the like. A preferred polymer to be utilized as the solvent is one in which at least about ten parts by volume of polymer will dissolve in one part by volume of water at 100° C.

$R_1$ and $R_2$ in Formula I may be alike or different and may be hydrogen or an alkyl group of from 1 to 20 carbon atoms. Where either or both of $R_1$ and $R_2$ are alkyl radicals, they are however preferably of from 1 to 10, especially 1 to 5, carbon atoms. Where both $R_1$ and $R_2$ are alkyl radicals, they may be alike or different. It would appear that those polymers of Formula I which are hydrophillic in nature, or partially hydrophillic, would not be satisfactory as a solvent utilized to absorb a carboxylic acid from mixtures thereof with water; such, however, have been found to perform satisfactorily. When utilizing any of the polymers of Formula I as a solvent, some small amounts of water will be absorbed and/or condensed into the polymer solvent but such can be easily removed, if desired, by distillation as hereinafter disclosed.

The polymer utilized as the solvent in accordance with the present invention must be one which is liquid under the conditions of the absorption and thus should not be of such a molecular weight as to be a solid, nor of so low a molecular weight as to vaporize at the temperatures involved in the absorption. In an industrial process, the viscosity of the polymer should also be such that it may be easily pumped at the temperatures involved. The molecular weight of the polymer should generally be within the range of about 250–5,000, preferably 300–2,000. The viscosity of the polymer, which has some relation to the molecular weight, should generally be within the range of about 1 to 200, preferably 2 to 60, centistokes at 99° C. The higher molecular weight polymers, that is those having a viscosity on the order of 60 to 100 centistokes at 99° C., will of course be more suitable at the higher temperatures than at the lower temperatures.

The carboxylic acids which may be recovered in accordance with the present invention are generally those known as the $C_2$–$C_6$ carboxylic acids, that is those carboxylic acids containing from 2 to 6 carbon atoms composed only of carbon, hydrogen and oxygen. These carboxylic acids may be either monocarboxylic or dicarboxylic acids and may be either saturated or unsaturated, the invention being especially useful in the recovery of saturated or monoethylenically unsaturated $C_2$–$C_5$ monocarboxylic acids. As to dicarboxylic acids, the invention is best suited for the $C_2$–$C_6$ saturated dicarboxylic acids or maleic acid. Where several of these carboxylic acids are contained in the gaseous mixture, all of them will be absorbed into the polymer solvent. The invention is especially useful in recovering acrylic acid and methacrylic acid. Other specific acids which may be recovered include acetic, propionic, butyric, isobutyric, maleic, oxalic, malonic, succinic, glutaric and adipic.

The present invention may be applied to gaseous mixtures containing carboxylic acids and water in practically any proportion, and, various other compounds and materials may also be present without adversely affecting the operation. Included among such other materials are inert gases, such as nitrogen, helium, carbon dioxide, carbon monoxide and oxygen, and intermediate oxygenated hydrocarbons such as alcohols, aldehydes and ketones. Generally speaking, the present invention is best applied to gaseous mixtures containing at least 0.1% by volume of carboxylic acid and containing an amount of water which, by volume, is at least one-twentieth (1/20) of the amount of the carboxylic acid present. The invention finds its best application in the treating of gaseous mixtures containing from about 0.3 to about 5.0% by volume of carboxylic acid, especially gaseous mixtures which are the reaction product of a vapor phase oxidation of a hydrocarbon or oxygenated hydrocarbon to produce a carboxylic acid product, more especially those processes wherein the compound being oxidized contains from 3 to 5 carbon atoms so as to produce a carboxylic acid product (including mixtures of carboxylic acids) containing from 2 to 5 carbon atoms.

The first step in obtaining an anhydrous carboxylic acid from the gaseous mixture is a gas absorption step wherein the gaseous mixture is intimately contacted with the liquid solvent. The intimate contact may be achieved by utilizing conventional gas absorption techniques and conventional equipment, the particular method of achieving such not being a part of the present invention. The most preferred method of achieving the intimate contact is by countercurrent contact of the gaseous mixture and the solvent in an absorption tower. The tower may be of the packed type or the tray or plate type, the tray or plate type being preferred. Such a tower should be such as to provide at least about 2, and preferably at least about 5, theoretical stages. A typical tower may for example contain from about 20 to 70 actual sieve trays. The gaseous mixture will be fed to the bottom of the tower and allowed to bubble upwardly through the descending liquid solvent introduced to the top of the tower.

The amount of solvent utilized should be such that the resulting acid enriched solvent fraction withdrawn from the tower contains at least about 2%, and preferably 5 to 25%, by weight of carboxylic acid. The maximum amount achievable will depend on the size of the absorption zone, temperature and pressure thereof, amount of water absorption that can be tolerated, and the like. The amount of water in the acid enriched solvent fraction will, however, preferably be very small, that is such that the amount of water therein is less than about 5% by weight of the weight of acid therein. If the gaseous mixture being treated contains inerts, such as nitrogen, and/or intermediate oxygenated hydrocarbons, such as alcohols, aldehydes and ketones, then small amounts of these inerts and intermediates will also be absorbed into the solvent. Most of such inerts and intermediates will however not be absorbed and will remain in the gaseous phase.

The temperature in the gas absorption zone where the intimate contact of gas and liquid is accomplished must be maintained such that, during the contact between the gaseous mixture and the liquid solvent, the water vapor in the gaseous mixture does not condense, and such that the solvent remains liquid. This is accomplished by maintaining the temperature below the boiling point of the solvent at the pressure involved, and above the dew point of the gaseous mixture at the pressure involved. In this regard, pressure is not critical and selection of a pressure at which to accomplish the intimate contact will largely depend on economics. The pressure may for example range from 0.5 to 50 atmospheres absolute, although pressures outside this range may also be used.

Generally speaking, the temperature during the absorption should be maintained within a few degrees above the dew point of the gaseous mixture. Increasing the temperature will cause less water to be absorbed, however such will also cause less carboxylic acid to be absorbed. In picking a temperature at which to operate, one must thus balance the increased carboxylic acid loss at the higher temperatures against the increased water absorption at the lower temperatures. It has been found that operation within the range of about 0.5° to 5° C. above the dew point of the gaseous mixture will provide a satisfactory balance between acid loss and water absorption. The invention is not, however, to be interpreted as limited to such since, in some processes, water absorption will not be of special concern while in other processes the amount of water absorption will necessarily have to be kept as low as possible even at the risk of losing acid.

After accomplishing the intimate contact of the gaseous mixture and the solvent, there will be obtained a liquid solvent fraction enriched in carboxylic acid. This solvent fraction may be treated by conventional techniques to recover the carboxylic acid therefrom. Preferably the carboxylic acid is recovered by distillation. Where, because of the particular solvent utilized or the conditions of the absorption, unacceptably high (although only a small percentage of the total) amounts of water have been absorbed into the solvent, the enriched solvent fraction is preferably first treated by extractive distillation to remove the water. Inert stripping may be utilized in connection with the extractive distillation. Such an extractive distillation may be accomplished by passing the acid enriched liquid solvent fraction to a distillation tower wherein liquid, lean solvent (such being the same solvent as utilized in the gas absorption) is introduced to the top of the extractive distillation column as the extractive liquid. Water and any residual amounts of inerts and oxygenated hydrocarbon intermediates contained in the enriched solvent fraction pass to the extractive distillation column will be removed overhead as vapors. Withdrawn from the lower portion of the extractive distillation column will be a substantially anhydrous solvent fraction containing the carboxylic acid dissolved therein, and which may be treated by flash distillation to separate the solvent from the carboxylic acid. In the flash distillation, the substantially anhydrous carboxylic acid product will be removed as overhead vapors and the solvent as bottoms product. This solvent may be recycled for use in the gas absorption and/or in the extractive distillation. Generally a purge of the recycled solvent will be necessary to prevent a build-up of impurities.

If the recovered substantially anhydrous carboxylic acid product comprises a mixture of carboxylic acids, they may be separated from each other by known methods.

Other distillation schemes and other recovery schemes may be utilized. For example the extractive distillation may be replaced or supplemented with a desorber in which the residual water, residual inerts and residual oxygenated hydrocarbon intermediates are expelled by countercurrent contact with a stripping gas such as air or nitrogen. A reboiled stripper may also be used. Other methods are known and will also be apparent to those skilled in the art. Stabilizers may be added in the recovery system if necessary, the need for such depending in a large part on the particular carboxylic acid or acids being recovered.

Reference is hereby made to the accompanying drawing for a more detailed description of a special embodiment of the invention. A gaseous mixture containing carboxylic acid and water, and also containing inert gases and intermediate oxygenated hydrocarbons is introduced to absorption column 10 through line 11. Solvent is introduced into the upper end of absorption column 10 through line 12, water also being introduced through line 13. The purpose of the water introduced through line 13 is to aid in controlling the temperature in absorption column 10 and such cooling can be accomplished by other means if desired. The solvent introduced through line 12 is derived from recycled solvent from line 14 and fresh, make-up solvent from line 15. Removed overhead of absorption column 10 is a gas comprising most of the water contained in the gaseous mixture introduced through line 11, as well as most of the inerts, intermediate oxygenated hydrocarbons, etc. introduced through line 11.

Withdrawn through line 16 and passed to extractive distillation tower 17 is a liquid, solvent fraction enriched in carboxylic acid, and, which contains small residual amounts of water, inerts and intermediate oxygenated hydrocarbons. Introduced through line 18 through the upper end of extractive distillation tower 17 as the extractive liquid is a solvent which is of the same composition as that utilized in the absorption. Removed overhead of extractive distillation tower 17 through line 19 is a gas containing substantially all of the residual water introduced to tower 17 as well as substantially all of any residual inerts and intermediate oxygenated hydrocarbons introduced to tower 17.

Removed from the bottom of extractive distillation tower 17 through line 20 and passed to flash distillation tower 21 is a substantially anhydrous, liquid, solvent fraction containing the desired carboxylic acid therein. The substantially anhydrous carboxylic acid product is removed as overhead vapors through line 22. Lean solvent is removed as liquid bottoms product through line 14 and recycled except for a small amount which is purged through line 23 to prevent buildup of impurities.

The following examples are given to more fully illustrate the present invention, but are not to be taken as limiting the scope thereof.

EXAMPLE I

A laboratory apparatus was constructed corresponding to the schematic flowsheet of the drawing. Absorption column 10 constituted a 2 inch diameter column which was 72 inches in height and contained 30 sieve trays. Extractive distillation tower 17 consisted of a 2 inch diameter column which was 110 inches in height and contained 55 trays. The flash distillation tower was a falling film evaporator (2 inches i.d. by 12 inches) heated by heat transfer oil. Such apparatus was used for the recovery of a substantially anhydrous methacrylic acid product from a gaseous mixture consisting of, in weight percent, about 6.8% methacrylic acid, 2.0% acetic acid, 31% water, traces of other liquids and 60% noncondensible gases.

The gaseous mixture at a temperature of 120° C. was passed to the base of absorption column 10 at a rate of 41.7 grams per minute with absorption column 10 being maintained at a temperature of about 80° C. overhead and a base temperature of 105° C. and a pressure of 960 mmHgA. Water having a temperature of about 52° C. was passed at a rate of 3.1 grams per minute through line 13 while about 20.6 grams per minute of solvent having a temperature of about 82° C. was fed through line 12. The solvent was a monobutyl ether of a mixed polyoxyethylene-polyoxypropylene glycol having a viscosity of 12 centistokes at 99° C., such being a commercially available product sold under the name "UCON HB-260" by Union Carbide Corporation.

Removed overhead of column 10 at a rate of about 40.5 grams per minute was a gas stream containing most of the water introduced into the absorption column as well as most of the inerts and trace amounts of by-products contained in the gaseous mixture fed through line 11. Removed as a liquid bottom stream through line 16 was a solvent fraction enriched in methacrylic acid and containing, in weight percent, about 11.4% methacrylic acid, 3.2% water, and 3.4% acetic acid, the remainder comprising solvent.

The enriched solvent fraction removed through line 16 was passed through the 25th tray of extractive distillation tower 17 having 55 trays total, which was maintained at a temperature of about 140° C. and a pressure of 125 mmHgA. Solvent having a temperature of 52° C. was passed through the upper end of column 17 through line 18 at a rate of about 8.7 grams per minute. Removed overhead of the extractive distillation tower through line 19 at a rate of 0.7 grams per minute was a gaseous stream containing substantially all of the residual water introduced to the extractive distillation tower as well as substantially all of the residual inerts and intermediate oxygenated hydrocarbons introduced to the extractive distillation tower.

Recovered as a liquid bottom stream through line 20 at a rate of 33 grams per minute was a solvent fraction consisting substantially of the solvent having the methacrylic acid product therein, and containing, in weight percent about 88.6% solvent, 8.6% methacrylic acid and 2.6% acetic acid and 0.2% water. This stream was then passed to flash tower 21 operated at 200° C. and a pressure of 30 mmHgA to flash the substantially anhydrous methacrylic overhead, such being removed through line 22 at a rate of about 3.7 grams per minute. The methacrylic acid product so recovered contained only about 1.8% by weight of water. The solvent recovered through line 14 contained about 1% by weight residual acid and was recycled as indicated in the drawing.

EXAMPLE II

The apparatus of Example I was used for the recovery of a substantially anhydrous methacrylic acid product from a gaseous mixture consisting of, in weight percent, about 5.9% methacrylic acid, 2.6% acetic acid, 31.7% water, traces of other liquid components and about 60% noncondensible gases.

The gaseous mixture at a temperature of 196° C. was passed to the base of absorption column 10 at a rate of 38.3 grams per minute, with absorption column 10 being maintained at a temperature of about 93° C. overhead and 115° C. at the base, and a pressure of 960 mmHgA. Water having a temperature of about 46° C. was passed at a rate of 3.1 grams per minute through line 13 while about 21.5 grams per minute of solvent having a temperature of about 38° C. was fed through line 12. The solvent was a straight chain polyoxyethylene glycol having a viscosity of 10.5 centistokes at 99° C. such being a commercially available product sold as "Carbowax 600" by Union Carbide Corporation.

Removed overhead of column 10 at a rate of about 35.8 grams per minute was a gas stream containing most of the water introduced into the absorption column as well as most of the inerts and trace amounts of by-products contained in the gaseous mixture fed through line 11. Removed as a liquid bottom stream through line 16 was a solvent fraction enriched in methacrylic acid and containing, in weight percent, about 6.8% methacrylic acid, 9.1% water, 3.2% acetic acid with the remainder comprising solvent.

The enriched solvent fraction removed through line 16 was passed through the 25th tray of extractive distillation tower 17 which was maintained at a temperature of about 121° C. and a pressure of 150 mmHgA. Solvent having a temperature of 54° C. was passed through the upper end of column 17 through line 18 at a rate of about 11.0 grams per minute. Removed overhead of the extractive distillation tower through line 19 at a rate of 3.1 grams per minute was a gaseous stream containing substantially all of the residual water introduced to the extractive distillation tower as well as substantially all of the residual inerts and intermediate oxygenated hydrocarbons introduced to the extractive distillation tower.

Recovered as a liquid bottom stream through line 20 at a rate of 41.6 grams per minute was a solvent fraction consisting substantially of the solvent having the methacrylic acid product therein, and containing, in weight percent about 92% solvent, 5.0% methacrylic acid and 0.1% water and 2.7% acetic acid. This stream was then passed to flash tower 21 operated at 214° C. and a pressure of 30 mmHgA to flash the substantially anhydrous methacrylic acid overhead, such being removed through line 22 at a rate of about 2.6 grams per minute. The methacrylic acid product so recovered contained only about 2% by weight of water. The solvent recovered through line 14 contained about 1.5% by weight residual acid and was recycled as indicated in the drawing.

The embodiments of the invention in which an exclusive property or privilege is claimed are defined as follows:

1. A process for recovering a $C_2$-$C_6$ carboxylic acid from a gaseous mixture comprising said carboxylic acid and water, said carboxylic acid being a monocarboxylic acid or a dicarboxylic acid and being composed only of carbon, hydrogen and oxygen, said process comprising: (a) in a gas absorption zone, intimately contacting said gaseous mixture, while maintained in the vapor phase, with a solvent which is maintained in the liquid phase whereby $C_2$-$C_6$ carboxylic acid is absorbed from said gaseous mixture into said solvent, said solvent comprising a polymer of the formula:

$$R_1-O-(X)-R_2 \qquad \text{I}$$

wherein $R_1$ and $R_2$ may be alike or different and are hydrogen or alkyl groups of 1 to 20 carbon atoms, and wherein X is a divalent polyoxyalkylene radical consisting essentially of repeating oxyalkylene units of the formula:

$$-(CH_2-CH-O)- \qquad \text{II}$$
$$\qquad \quad |$$
$$\qquad \, R_3$$

wherein $R_3$ is hydrogen or a lower alkyl radical of from 1 to 6 carbon atoms and wherein $R_3$ may be alike or different on the repeating oxyalkylene units, said polymer having a molecular weight within the range of about 250 to 5,000, the intimate contact of said gaseous mixture and said solvent being accomplished at a temperature which is below the boiling point of said solvent at the pressure involved and which is above the dew point of said gaseous mixture at the pressure involved so as to prevent condensation of the water from said gaseous mixture; and, (b) removing from said gas absorption zone a liquid, acid enriched solvent fraction consisting essentially of said solvent having $C_2$-$C_6$ carboxylic acid absorbed therein, and recovering $C_2$-$C_6$ carboxylic acid from said solvent fraction.

2. The process of claim 1 wherein said $C_2$-$C_6$ carboxylic acid is a $C_2$-$C_5$ monocarboxylic acid, and wherein $R_3$ may be alike or different on the repeating oxyalkylene units.

3. The process of claim 2 wherein $R_3$ is hydrogen such that X consists of repeating oxyethylene units, said solvent being hydrophillic.

4. The process of claim 3 wherein $R_1$ is a lower alkyl radical of from 1 to 5 carbon atoms and $R_2$ is hydrogen or a lower alkyl radical of from 1 to 5 carbon atoms.

5. The process of claim 3 wherein both $R_1$ and $R_2$ are hydrogen such that said polymer is a polyoxyethylene glycol.

6. The process of claim 2 wherein from about 10 to 90% of said repeating oxyalkylene units are oxyethylene units wherein $R_3$ is hydrogen, and the remaining 10 to 90% of said repeating oxyalkylene units are oxypropylene units wherein $R_3$ is methyl.

7. The process of claim 6 wherein $R_1$ is a lower alkyl radical of from 1 to 5 carbon atoms, wherein $R_2$ is hydrogen or a lower alkyl radical of from 1 to 5 carbon atoms, said polymer being one wherein at least about ten parts by volume of polymer will dissolve in one part by volume of water at 100° C.

8. The process of claim 7 wherein said divalent polyoxyalkylene radical consists of a random mixture of said oxyethylene units and said oxypropylene units.

9. The process of claim 8 wherein $R_1$ is a lower alkyl radical of from 1 to 5 carbon atoms and $R_2$ is hydrogen.

10. The process of claim 9 wherein said polymer has a viscosity at 99° C. within the range of about 2 to 60 centistokes.

11. The process of claim 2 wherein $R_3$ is methyl such that X consists of repeating oxypropylene units, said polymer being hydrophobic.

12. The process of claim 11 wherein $R_1$ is a lower alkyl radical of from 1 to 5 carbon atoms, wherein $R_2$ is hydrogen or a lower alkyl radical of from 1 to 5 carbon atoms.

13. The process of claim 1 wherein said $C_2$-$C_6$ carboxylic acid is a saturated $C_2$-$C_6$ dicarboxylic acid or maleic acid, wherein $R_3$ is hydrogen or a methyl radical, and wherein $R_3$ may be alike or different on the repeating oxyalkylene units, wherein $R_1$ is hydrogen or a lower alkyl radical of from 1 to 5 carbon atoms and wherein $R_2$ is hydrogen or a lower alkyl radical of from 1 to 5 carbon atoms.

14. The process of claim 13 wherein $R_3$ is hydrogen such that X consists of repeating oxyethylene units.

15. The process of claim 14 wherein $R_2$ is hydrogen.

16. The process of claim 13 wherein from about 10 to 90% of said repeating oxyalkylene units are oxyethylene units wherein $R_3$ is hydrogen, and the remaining 10 to 90% of said repeating oxyalkylene units are oxypropylene units wherein $R_3$ is methyl.

17. The process of claim 16 wherein $R_2$ is hydrogen.

18. The process of claim 13 wherein said $C_2$-$C_6$ dicarboxylic acid is a saturated $C_2$-$C_6$ dicarboxylic acid.

19. The process of claim 13 wherein said $C_2$-$C_6$ carboxylic acid is maleic acid.

20. The process of claim 1 wherein in step (b) thereof, the liquid, acid enriched solvent fraction consisting essentially of said solvent having $C_2$-$C_6$ carboxylic acid absorbed therein is passed to an extractive distillation column for removal of residual amounts of water therefrom, the extraction agent utilized in said extractive distillation column being said solvent, there being withdrawn from the lower portion of said extractive distillation column a substantially anhydrous solvent fraction enriched in $C_2$-$C_6$ carboxylic acid, and, recovering the $C_2$-$C_6$ carboxylic acid therefrom by distillation.

* * * * *